(12) United States Patent
Marzolf

(10) Patent No.: US 12,667,510 B2
(45) Date of Patent: Jun. 30, 2026

(54) KNEE JOINT REHABILITATION ASSIST DEVICE AND METHOD

(71) Applicant: Kneewell, LLC, Minnetonka, MN (US)

(72) Inventor: William Marzolf, Minnetonka, MN (US)

(73) Assignee: Kneewell, LLC, Minnetonka, MN (US)

( * ) Notice: Subject to any disclaimer, the term of this patent is extended or adjusted under 35 U.S.C. 154(b) by 378 days.

(21) Appl. No.: 18/083,146

(22) Filed: Dec. 16, 2022

(65) Prior Publication Data

US 2024/0197514 A1     Jun. 20, 2024

(51) Int. Cl.
  *A61H 1/02*     (2006.01)
  *A61F 5/042*    (2006.01)
(52) U.S. Cl.
  CPC .............. *A61H 1/024* (2013.01); *A61F 5/042* (2013.01)
(58) Field of Classification Search
  CPC ........ A61H 1/02; A61H 1/0237; A61H 1/024; A61F 5/04; A61F 5/042
  See application file for complete search history.

(56) References Cited

U.S. PATENT DOCUMENTS

| | | | | |
|---|---|---|---|---|
| 4,784,121 | A | * | 11/1988 | Brooks ............ A63B 23/03583 |
| | | | | 482/131 |
| 4,844,454 | A | * | 7/1989 | Rogers ................... A61H 1/024 |
| | | | | 482/131 |
| 5,236,333 | A | * | 8/1993 | Barba, Jr. .............. A61H 1/024 |
| | | | | 602/5 |
| 6,962,570 | B2 | * | 11/2005 | Callanan ................ A61H 1/024 |
| | | | | 601/5 |
| 7,309,305 | B2 | * | 12/2007 | Nichols ............ A63B 21/00047 |
| | | | | 482/148 |
| 7,534,213 | B2 | * | 5/2009 | Shelbourne ............ A61H 1/024 |
| | | | | 601/5 |
| 9,492,342 | B2 | * | 11/2016 | Hall ........................ A61H 1/008 |
| 10,123,927 | B2 | * | 11/2018 | Gilderman ....... A63B 21/00185 |
| 11,083,662 | B2 | * | 8/2021 | Marti ............... A63B 21/00185 |
| 11,116,686 | B2 | * | 9/2021 | Kramer ................ A63B 21/068 |
| 11,324,624 | B2 | * | 5/2022 | Slishman ................ A61F 5/048 |
| 2009/0017995 | A1 | * | 1/2009 | Freiberg ........... A63B 21/00181 |
| | | | | 482/91 |
| 2016/0317084 | A1 | * | 11/2016 | DeLuke ............. A61B 17/7037 |
| 2020/0197251 | A1 | * | 6/2020 | Shelbourne .............. A61H 1/02 |

* cited by examiner

*Primary Examiner* — Keri J Nelson
(74) *Attorney, Agent, or Firm* — Schwegman Lundberg & Woessner, P.A.

(57) ABSTRACT

A knee joint rehabilitation assist device and associated methods are shown. A knee joint rehabilitation assist device includes a rigid frame, a heel rest attached across one end of the frame to accommodate a heel of a user, and a knee contact attached at a distance spaced from the heel rest. Adjustability of various components and a ratcheting pressure control provide gradual controllable pressure to increase range of motion in a knee joint.

4 Claims, 5 Drawing Sheets

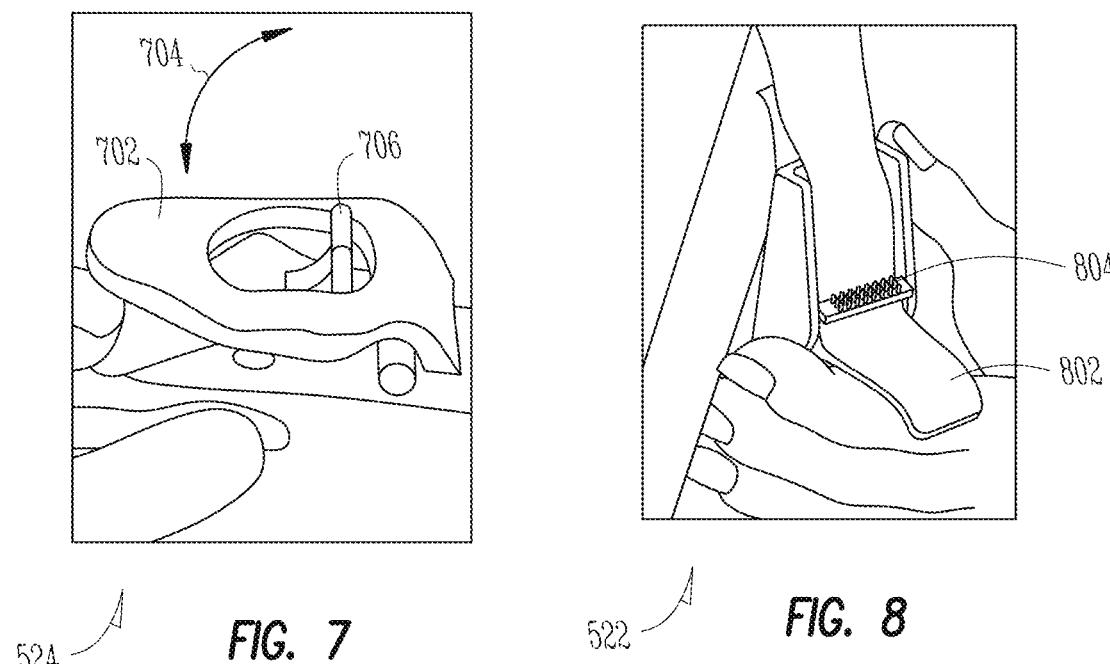
FIG. 7
FIG. 8
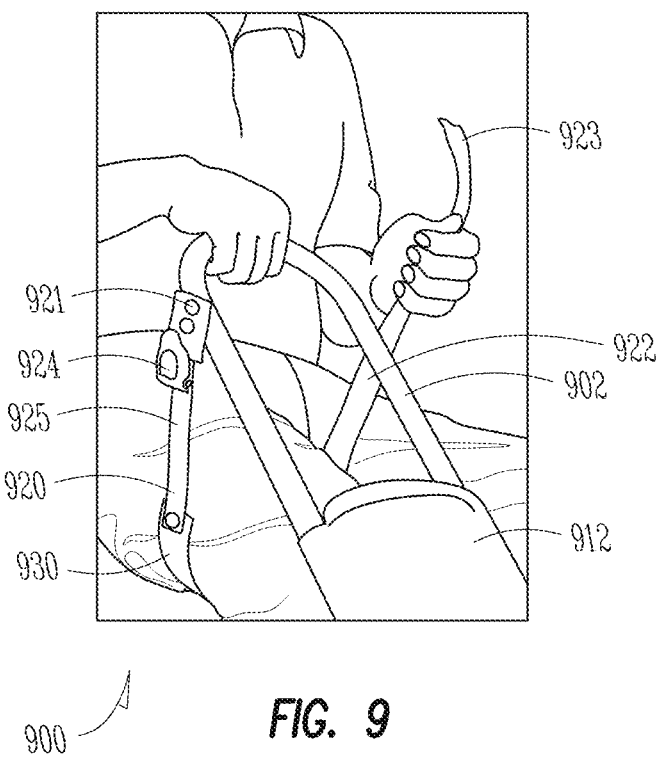
FIG. 9

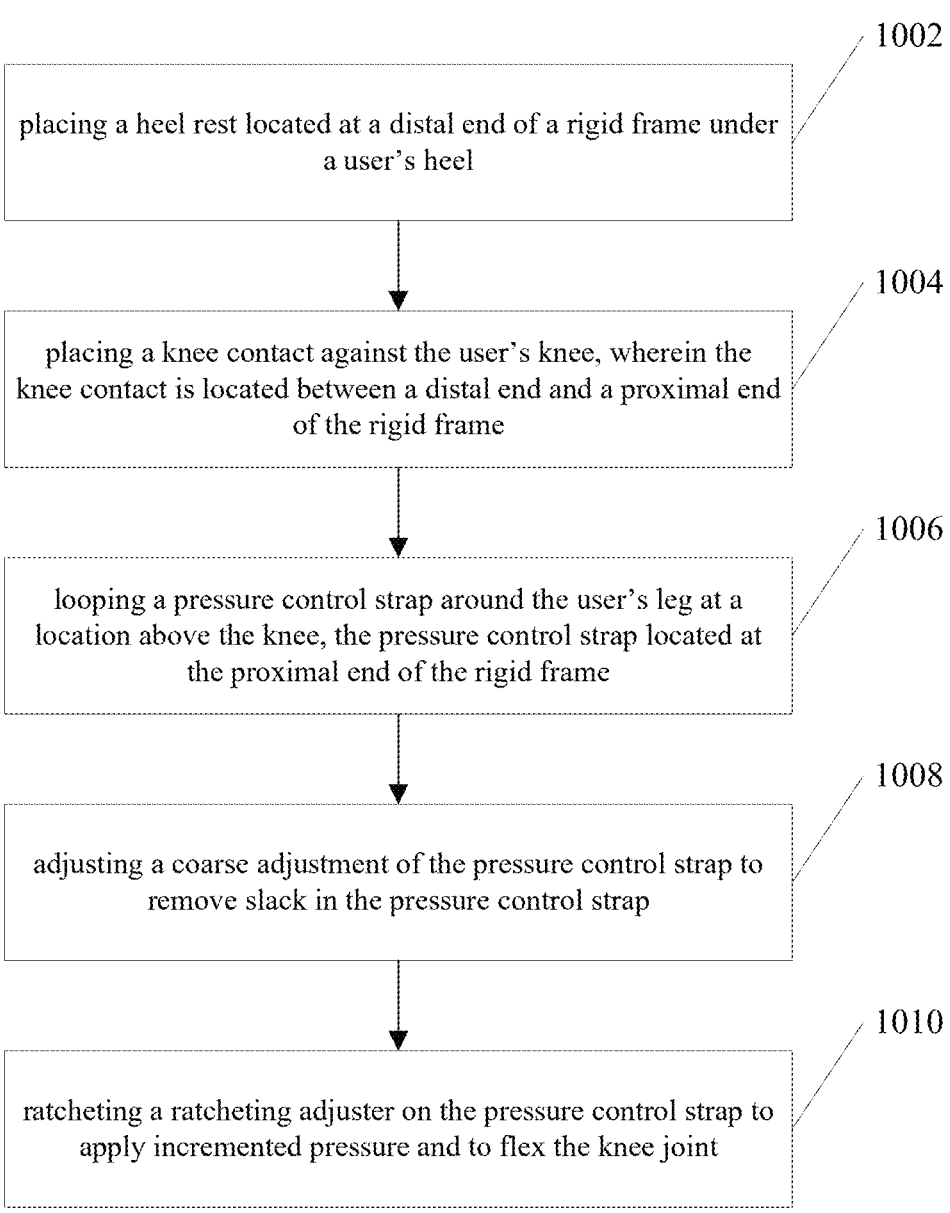

placing a heel rest located at a distal end of a rigid frame under a user's heel

1002 placing a knee contact against the user's knee, wherein the knee contact is located between a distal end and a proximal end of the rigid frame

1004 looping a pressure control strap around the user's leg at a location above the knee, the pressure control strap located at the proximal end of the rigid frame

1006 adjusting a coarse adjustment of the pressure control strap to remove slack in the pressure control strap

1008 ratcheting a ratcheting adjuster on the pressure control strap to apply incremented pressure and to flex the knee joint

KNEE JOINT REHABILITATION ASSIST DEVICE AND METHOD

BACKGROUND

The present invention relates generally to orthopedic devices and, in particular, to a device used in the exercising of a knee following injury or surgery, particularly to aid in the rehabilitation process following a total knee replacement. Adjustability of devices is important to ensure proper function of devices across a number of different body dimensions. Consistent gradual control of pressure is desired to improve operation of devices. It is desired to have orthopedic devices that address these concerns, and other technical challenges.

BRIEF DESCRIPTION OF THE DRAWINGS

FIG. 7 shows a ratcheting adjuster in accordance with some example embodiments.

FIG. 8 shows a coarse length adjuster in accordance with some example embodiments.

FIG. 9 shows another knee joint rehabilitation assist device in use in accordance with some example embodiments.

FIG. 10 shows a flow diagram of a method of rehabilitating a knee joint after surgery in accordance with some example embodiments.

DESCRIPTION OF EMBODIMENTS

The following description and the drawings sufficiently illustrate specific embodiments to enable those skilled in the art to practice them. Other embodiments may incorporate structural, logical, electrical, process, and other changes. Portions and features of some embodiments may be included in, or substituted for, those of other embodiments. Embodiments set forth in the claims encompass all available equivalents of those claims.

The following detailed description describes embodiments that include concepts of the present development. Those embodiments are meant as examples only and are not intended to limit the scope of the present invention in any manner as variations of the development will occur to those skilled in the art.

Figure 1:
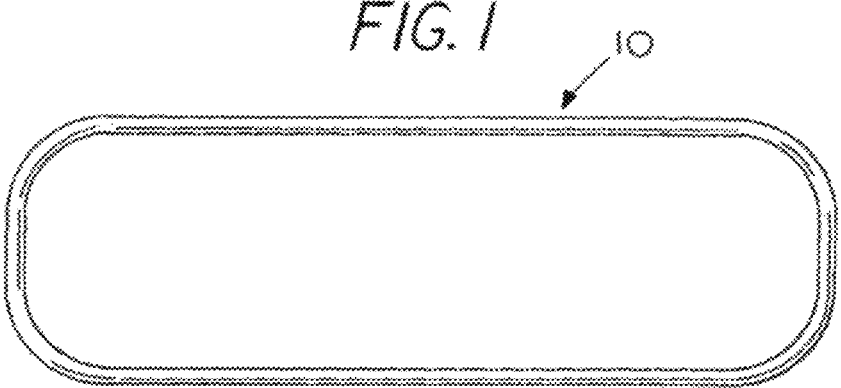
FIG. 1 shows a frame element in accordance with some example embodiments.

FIG. 1 depicts a generally rectangular tubing structure 10 which serves as the frame for the knee joint rehabilitation device of the invention. One such frame was made of 1 inch diameter aluminum tubing bent and welded to create a continuous generally rectangular structure. Of course, fasteners such as rivets may also be used. One such structure was 34 inches (86.36 cm) long by 10 inches (25.4 cm) wide. However, it will be appreciated that the frame can be any desired size and constructed of any useful rigid material. A 36 inch (91.4 cm) model and a 32 inch (81.28 cm) have also been demonstrated.

Figure 2:
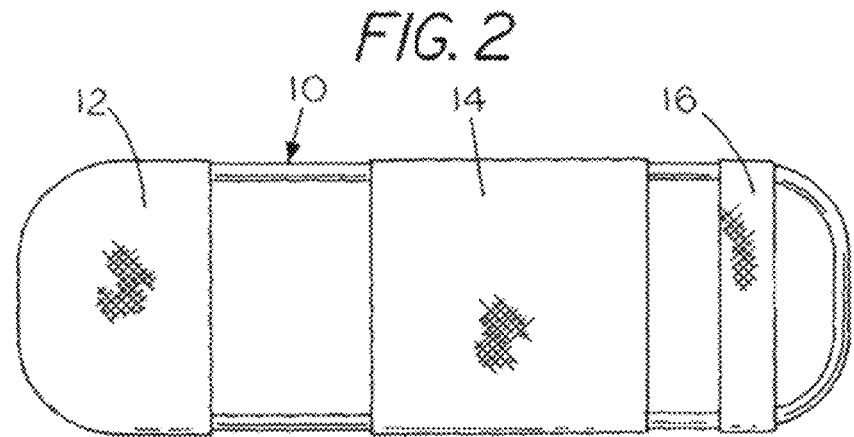
FIG. 2 shows a knee joint rehabilitation assist device in accordance with some example embodiments.
Figure 3:
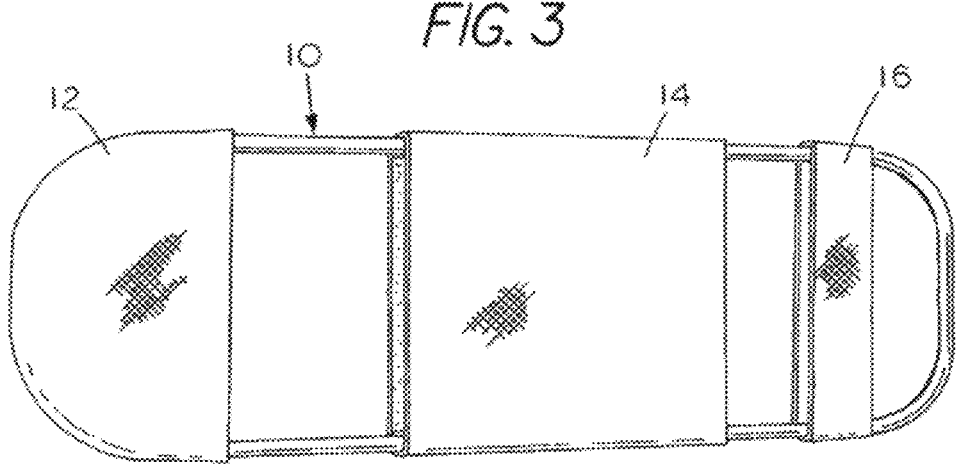
FIG. 3 shows a knee joint rehabilitation assist device in accordance with some example embodiments.

FIG. 2 is a schematic drawing showing the knee joint rehabilitation aid of the invention, including the frame 10 with the heel rest 12 located at one end of the frame. A knee contact 14 is shown intermediate the ends of the frame and it is configured so it is adjustable there along to accommodate the knee of the user depending on the distance between the heel and the knee. An adjustable pressure strap 16 is shown toward what becomes the upper end of the device fastened around the thigh of the user and over the upper end portion of the frame. A picture of an assembled device is shown in FIG. 3.

Figure 4:
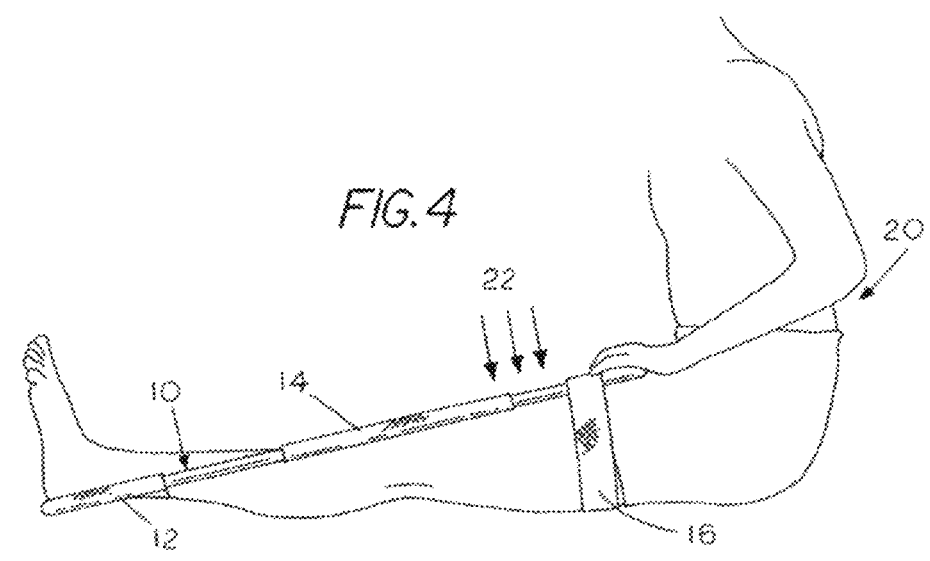
FIG. 4 shows a knee joint rehabilitation assist device in use in accordance with some example embodiments.

FIG. 4 depicts an embodiment of the knee joint rehabilitation aid of the invention as employed by a user 20. In use, the patient inserts the lower leg through the gap between the heel rest 12 and the knee contact 14 so that the heel is at or near what becomes the bottom of the device. The knee contact 14 can then be adjusted to meet the middle of the knee such that downward pressure on the sides of the upper portion of the frame stretches the leg toward full extension. The pressure strap 16 can then be tightened around the upper portion of the frame to adjust the tension on the leg and knee joint as desired as the amount of tension and, therefore, generally, the amount of pain endured by the patient depends on the amount of downward pressure 22 applied on the upper portion of the frame.

Figure 5:
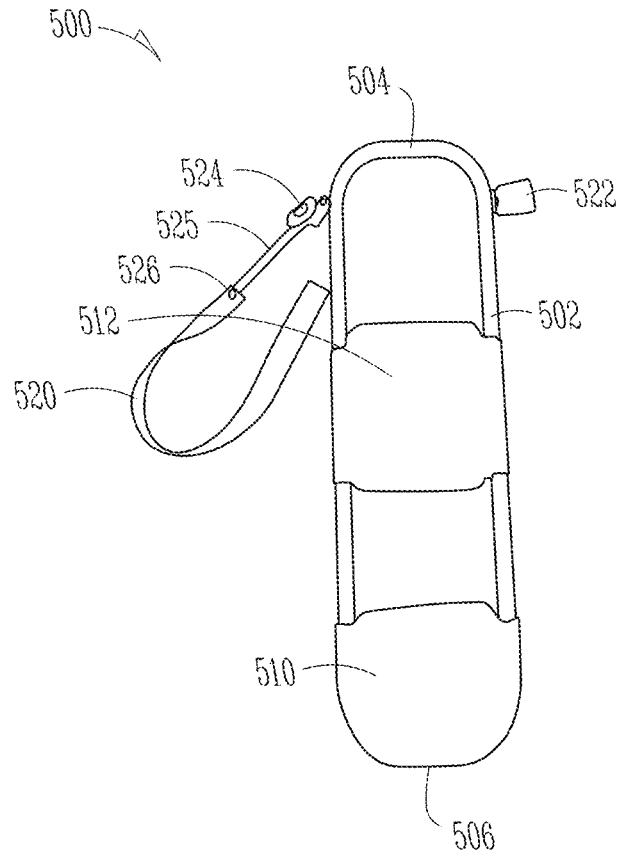
FIG. 5 shows another knee joint rehabilitation assist device in accordance with some example embodiments.

FIG. 5 shows another example of a knee joint rehabilitation assist device 500. The device 500 includes a rigid frame 502, having a proximal end 504 and a distal end 506. Examples of rigid frame materials include, but are not limited to, metals such as aluminum or steel, or rigid organic materials such as rigid plastics or carbon fiber reinforced composite materials. In one example, the rigid frame 502 has an adjustable length, as discussed in more detail below. A heel rest 510 is shown at the distal end 506 of the rigid frame 502. Other lower leg fixtures apart from a heel rest 510 are also within the scope of the invention. For example, an ankle strap or other fixture that provides the desired fulcrum action with respect to the knee contact 512 is also possible.

A knee contact 512 is shown located between the distal end 506 and the proximal end 504 of the rigid frame 502. The knee contact may include a flexible material such as fabric, and may include padding such as a polymer foam, felt, or other padding.

In one example, the knee contact 512 is movable within a range between the distal end and the proximal end. In one example, the adjustability of the knee contact 512 is provided by a configuration where the knee contact 512 is formed at least partially from a fabric or other flexible material that is positioned around the rigid frame 502, but is not directly attached to the rigid frame 502. In this way, the knee contact 512 is allowed to side back and forth within the range of motion between the proximal end 504 and the distal end 506. In one example, the knee contact 512 is formed to include two tunnels on either side of the knee contact 512, with portions of the rigid frame 502 passing through the tunnels. This configuration provides the desired range of adjustability, but also keeps the knee contact 512 from sliding off an end of the rigid frame 502. Other adjustable configurations of knee contact 512 include, but are not limited to a single wrap that encompasses the rigid frame 502 without forming tunnels.

In one example, the knee contact 512 may include a length of fabric or other flexible material with hook and loop fastener material adapted to form a wrap of material around the rigid frame 502. Using hook and loop fastener material permits a user to adjust a length of the knee contact 512, which in turn changes a geometry of the knee joint rehabilitation assist device 500 when in use. This allows different positioning of the proximal end 504 that may provide different leverage of force to a user.

FIG. 5 further shows a pressure control strap 520 located at the proximal end 504 of the rigid frame 502. In use, a user tightens or otherwise adjusts a length of the pressure control strap 520 to control downward pressure to an upper surface of the knee through the knee contact 512. In one example, the pressure control strap 520 includes a length of teeth 525 coupled to a length of fabric or other flexible strap at location 526.

The example of FIG. 5 further shows a coarse length adjuster 522 and a ratcheting adjuster 524. In one example, the coarse length adjuster includes a cam lock buckle, although the invention is not so limited. Other coarse length adjusters include, but are not limited to, hook and loop fasteners, ladder lock buckles, ladder lock buckles with side release, etc. A cam lock buckle provides a desirable combination of ease of use, and secure holding power. A cam lock buckle also provides an easy method to release all tension in the pressure control strap quickly if pain is too great for a user. By pulling down on a loose end of the pressure control strap, the cam lock buckle is opened, and pressure is quickly released.

In use, a user places their heel in the heel rest in an arrangement with the knee contact over their knee. The pressure control strap is then threaded through the coarse length adjuster and tightened to be snug against their leg. The coarse length adjuster is then actuated to hold the pressure control strap firm. Then the ratcheting adjuster is actuated by one or multiple ratchet teeth at a time to gradually tighten the pressure control strap in a controlled and predictable manner. Using the configuration of FIG. 5 as an example, the ratcheting adjuster 524 increments by one tooth in the length of teeth 525 with each actuation of the ratcheting adjuster 524. In this way, a user applies force to their knee joint to gradually straighten the joint under pressure. By using gradual control provided by the ratcheting adjuster 524, the user is able to slowly and controllably increase range of motion in the knee joint to facilitate recovery from knee replacement surgery. A number of ratchets advanced provides a user with an easy measure of how far (how many clicks) they are advancing to apply pressure. This can also be helpful when discussing use of the device with a coordinating physical therapist or doctor.

In one example, a force sensor is further included to measure a force applied to increase range of motion in the knee joint. One example of a force sensor includes a spring with an extension indicator located in line with the pressure control strap 520. Another example of a force sensor includes a pressure sensor underneath the knee contact or in the heel rest. Piezoelectric force sensors are within the scope of the invention. Another example of a force sensor includes a flex sensor incorporated into the rigid frame 502, such as a strain gauge. Advantages of a spring with an extension indicator located in line with the pressure control strap 520 include low cost, no need for a battery, and reliability.

Figure 6:
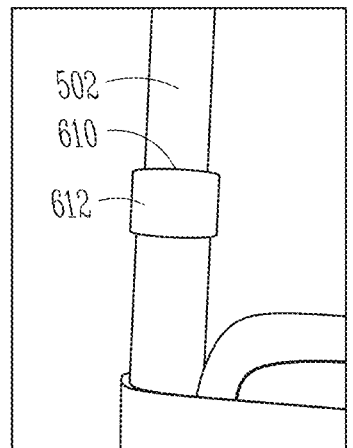
FIG. 6 shows a portion of a frame member in accordance with some example embodiments.

FIG. 6 shows a portion of the rigid frame 502 from FIG. 5. A telescoping joint 610 is shown to provide an adjustable length to the rigid frame 502. As shown in FIG. 5, in one example the rigid frame 502 includes a pair of frame members adapted for location on either side of a knee joint during operation. In such a configuration, a pair of telescoping joints are included in the pair of frame members. In the example of FIG. 6, a collet fastener 612 is further included to optionally lock and release the telescoping joint 610. A collet fastener uses a threaded collar to clamp on a number of wedged segments and lock a joint in place.

Although a collet fastener 612 and telescoping joint 610 are shown as an example to provide length adjustability to the rigid frame 502, the invention is not so limited. Other examples of joints and locking mechanisms include, but are not limited to, an array of holes and a pin or bolt, a rack and gear adjustment, etc. Although the rigid frame is shown as tubular, the invention is not so limited. Other cross sections such as square, U-shaped, etc. are also within the scope of the invention.

In use, due to different leg lengths of users, it is desirable to be able to adjust a length of the rigid frame 502. Although moving the knee contact between the distal end and the proximal end provides for different leg lengths between a heel and a knee, the additional adjustability of the frame length provides the ability to increase or decrease leverage when forcing the knee joint into increasing amounts of straightening.

FIG. 7 shows a close up view of one example of a ratcheting adjuster 524. In use, a lever 702 is actuated in a rotation as shown by arrows 704 to increment a length of the pressure control strap 520 one tooth at a time. A release lever 706 is further shown that when actuated, releases the ratcheting adjuster 524 to remove pressure on the knee joint.

FIG. 8 shows a close up view of one example of a coarse length adjuster 522. An actuator lever 802 is shown the is coupled to a cam 804. When rotated parallel to the pressure control strap 520, the actuator lever 802 drives the cam 804 into the pressure control strap 520 and holds it securely at a selected location.

FIG. 9 shows a knee joint rehabilitation assist device as described in use. As described above, a user places their heel in the heel rest in an arrangement with the knee contact 912 over their knee. A distal end 923 of the pressure control strap 920 is then threaded through the coarse length adjuster 922 and tightened to be snug against their leg. The coarse length adjuster 922 is then actuated to hold the pressure control strap 920 firm. Then the ratcheting adjuster 924 is actuated by one or multiple ratchet teeth at a time to gradually tighten the pressure control strap 290 in a controlled and predictable manner. As shown, a length of teeth 925 is coupled to the pressure control strap 920 at location 925. The ratcheting adjuster 924 is coupled to a rigid frame 902 at location 921.

The ratcheting adjuster 924 increments by one tooth in the length of teeth 925 with each actuation of the ratcheting adjuster 924. In this way, a user applies force to their knee joint to gradually straighten the joint under pressure. By using gradual control provided by the ratcheting adjuster 524, the user is able to slowly and controllably increase range of motion in the knee joint to facilitate recovery from knee replacement surgery. By adjusting a length of the rigid frame 902, a contact point 930 between the pressure control strap 920 and a user's leg can be adjusted which changes the amount of leverage in the knee joint rehabilitation assist device.

FIG. 10 shows one example of a flow diagram of a method of rehabilitating a knee joint after surgery. In operation 1002, a heel rest located at a distal end of a rigid frame is placed under a user's heel. In operation 1004, a knee contact is placed against the user's knee. In one example, the knee contact is located between a distal end and a proximal end of the rigid frame. In operation 1006, a pressure control strap is looped around the user's leg at a location above the knee.

In one example, the pressure control strap is located at the proximal end of the rigid frame. In operation 1008, a coarse adjustment of the pressure control strap is adjusted to remove slack in the pressure control strap. In operation 1010, a ratcheting adjuster is ratcheted on the pressure control strap to apply incremented pressure and to flex the knee joint.

It will be appreciated that examples of knee joint rehabilitation assist devices as described aid of the invention is a simple manual device that provides an important therapy to a patient following, for example, total knee arthroplasty (total knee replacement) or reconstructive knee surgery. When used as prescribed, the device will aid greatly to alleviate and return knee flexion contracture prevalent in all stages of the rehabilitation process with the aim being total extension of the knee joint or complete straightening of the leg. The device is designed to be used after the incision on the top of the knee is significantly healed (4-6 weeks) and the patient is able to put significant weight on the affected leg.

It will be recognized that the most common complication associated with the rehabilitation process following a TKR (total knee replacement) is the pain experienced during leg flexion exercises. The basic goal for rehabilitation is to attain 145° of flexion and 0° of flexion contracture or extension as that will allow the patient to achieve a normal walking gait and resume normal activities. The sheer pain involved in this therapy process makes some patients stop the rehabilitation process altogether before a normal walking gait is realized.

Waiting too long, on the other hand, not only makes it impossible to achieve a normal walking gait, but may also lead to associated problems with hips, back and continued knee pain. While knee joint rehabilitation assist devices shown do not remove the pain from the process, they do allow the patient to rehabilitate the knee at his or her own pace with as much or little pain as he can stand on any certain day. The device is designed to be used with the patient sitting on the edge of a chair or on the floor and, with the aid of the pressure control strap, can provide the desired constant soft tissue stretch, which is very important.

Because the device is operated manually, the patient decides just how much downward pressure to apply directly to the top of the knee joint in order to gain the last ten to fifteen degrees of gait flexion contracture. This thereby restores the full use of the leg and the normal walking gait. The process can be repeated for as long or as many times daily as the patient feels necessary, considering comfort level until 0° of flexion is achieved. The device is designed to be a secondary device used in conjunction with a full rehabilitation regimen.

An important aspect of the design of the device, including the rectangular shape of the frame, prevents a patient from putting too much downward pressure on the knee that may result in hyper-extension and possible damage to the healing joint. The top of the frame is designed to rest on the thigh before the joint goes past 20° or full straightening.

One material preferred to make the knee contact and the heel rest is cotton denim, however, this can be made of any desirable durable fabric. One heel rest used is a pouch containing about 1½ inches (3.8 cm) of foam rubber and has a top which folds over and is sealed with the hook and loop material. Likewise, the knee contact may also have 1½ inch (3.8 cm) foam rubber in the middle and be sealed with a hook and loop system which allows for easy removal and replacement of the foam if desired. Of course, other materials beside foam rubber are contemplated and any material having similar properties can be used.

To better illustrate the method and apparatuses disclosed herein, a non-limiting list of embodiments is provided here:

Example 1 includes a knee joint rehabilitation assist device. The device includes a rigid frame having an adjustable length, a lower leg fixture at a distal end of the rigid frame, a knee contact between the distal end and a proximal end of the rigid frame, wherein the knee contact is movable within a range between the distal end and the proximal end, and a pressure control strap located at the proximal end of the rigid frame, the pressure control strap configured to control downward pressure to an upper surface of the knee through the knee contact when in use.

Example 2 includes the device of example 1, wherein the lower leg fixture includes a heel rest.

Example 3 includes the device of any one of examples 1-2, wherein the rigid frame includes a pair of frame members adapted for location on either side of a knee joint during operation, and wherein the adjustable length is adjustable using a pair of telescoping joints in the pair of frame members.

Example 4 includes the device of any one of examples 1-3, wherein the pair of telescoping joints further include fasteners to optionally fix a selected length of the rigid frame.

Example 5 includes the device of any one of examples 1-4, wherein the fasteners include collet fasteners.

Example 6 includes the device of any one of examples 1-5, further including a ratcheting adjuster on the pressure control strap to control a length of the pressure control strap in ratcheted increments.

Example 7 includes the device of any one of examples 1-6, further including a coarse length adjuster to operate in combination with the ratcheting adjuster.

Example 8 includes the device of any one of examples 1-7, wherein the coarse length adjuster includes a cam lock buckle within a portion of the pressure control strap.

Example 9 includes the device of any one of examples 1-8, further including a force sensor within a portion of the pressure control strap.

Example 10 includes the device of any one of examples 1-9, wherein the rigid frame includes aluminum metal.

Example 11 includes the device of any one of examples 1-10, wherein the rigid frame includes metal tubing.

Example 12 is a knee joint rehabilitation assist device. The device includes a rigid frame having an adjustable length, a heel rest at a distal end of the rigid frame, a knee contact between the distal end and a proximal end of the rigid frame, wherein the knee contact is movable within a range between the distal end and the proximal end, a pressure control strap located at the proximal end of the rigid frame, the pressure control strap configured to control downward pressure to an upper surface of the knee through the knee contact when in use, and a ratcheting adjuster on the pressure control strap to control a length of the pressure control strap in ratcheted increments.

Example 13 includes the device of Example 12, further including a coarse length adjuster to operate in combination with the ratcheting adjuster.

Example 14 includes the device of any one of Examples 12-11, wherein the coarse length adjuster includes a cam lock buckle within a portion of the pressure control strap.

Example 15 includes the device of any one of Examples 12-14, wherein the rigid frame includes aluminum metal.

Example 16 includes the device of any one of Examples 12-15, wherein the rigid frame includes metal tubing.

Example 17 includes the device of any one of Examples 12-16, wherein the knee contact includes a fabric sling that is large enough to cover an entire knee joint.

Example 18 is a method of rehabilitating a knee joint after surgery. The method includes placing a heel rest located at a distal end of a rigid frame under a user's heel, placing a knee contact against the user's knee, wherein the knee contact is located between a distal end and a proximal end of the rigid frame, looping a pressure control strap around the user's leg at a location above the knee, the pressure control strap located at the proximal end of the rigid frame, adjusting a coarse adjustment of the pressure control strap to remove slack in the pressure control strap, and ratcheting a ratcheting adjuster on the pressure control strap to apply incremented pressure and to flex the knee joint.

Example 19 includes the method of Example 18, further including adjusting a length of the rigid frame to place the proximal end of the rigid frame above the knee joint.

Example 20 includes the method of any one of Examples 18-19, wherein adjusting a length of the rigid frame includes sliding one or more telescoping joints within a range of motion, and tightening the one or more telescoping joints at a selected length.

Example 21 includes the method of any one of Examples 18-20, wherein tightening the one or more telescoping joints at a selected length includes threading one or more collets into a locked position.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Although an overview of the inventive subject matter has been described with reference to specific example embodiments, various modifications and changes may be made to these embodiments without departing from the broader scope of embodiments of the present disclosure. Such embodiments of the inventive subject matter may be referred to herein, individually or collectively, by the term "invention" merely for convenience and without intending to voluntarily limit the scope of this application to any single disclosure or inventive concept if more than one is, in fact, disclosed.

The embodiments illustrated herein are described in sufficient detail to enable those skilled in the art to practice the teachings disclosed. Other embodiments may be used and derived therefrom, such that structural and logical substitutions and changes may be made without departing from the scope of this disclosure. The Detailed Description, therefore, is not to be taken in a limiting sense, and the scope of various embodiments is defined only by the appended claims, along with the full range of equivalents to which such claims are entitled.

As used herein, the term "or" may be construed in either an inclusive or exclusive sense. Moreover, plural instances may be provided for resources, operations, or structures described herein as a single instance. Additionally, boundaries between various resources, operations, modules, engines, and data stores are somewhat arbitrary, and particular operations are illustrated in a context of specific illustrative configurations. Other allocations of functionality are envisioned and may fall within a scope of various embodiments of the present disclosure. In general, structures and functionality presented as separate resources in the example configurations may be implemented as a combined structure or resource. Similarly, structures and functionality presented as a single resource may be implemented as separate resources. These and other variations, modifications, additions, and improvements fall within a scope of embodiments of the present disclosure as represented by the appended claims. The specification and drawings are, accordingly, to be regarded in an illustrative rather than a restrictive sense.

The foregoing description, for the purpose of explanation, has been described with reference to specific example embodiments. However, the illustrative discussions above are not intended to be exhaustive or to limit the possible example embodiments to the precise forms disclosed. Many modifications and variations are possible in view of the above teachings. The example embodiments were chosen and described in order to best explain the principles involved and their practical applications, to thereby enable others skilled in the art to best utilize the various example embodiments with various modifications as are suited to the particular use contemplated.

It will also be understood that, although the terms "first," "second," and so forth may be used herein to describe various elements, these elements should not be limited by these terms. These terms are only used to distinguish one element from another. For example, a first contact could be termed a second contact, and, similarly, a second contact could be termed a first contact, without departing from the scope of the present example embodiments. The first contact and the second contact are both contacts, but they are not the same contact.

The terminology used in the description of the example embodiments herein is for the purpose of describing particular example embodiments only and is not intended to be limiting. As used in the description of the example embodiments and the appended examples, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

The invention claimed is:

1. A method of rehabilitating a knee joint after surgery comprising:

placing a heel rest located at a distal end of a rigid frame under a user's heel;

placing a knee contact against the user's knee, wherein the knee contact is located between the distal end and a proximal end of the rigid frame;

looping a pressure control strap around the user's leg at a location above the knee, wherein a loop of the pressure control strap presses against a lower portion of the user's leg and is open on an upper portion of the user's leg, the pressure control strap located at the proximal end of the rigid frame;

adjusting a coarse adjustment of the pressure control strap to remove slack in the pressure control strap; and ratcheting a ratcheting adjuster on the pressure control strap to apply incremented pressure to the lower portion of the user's leg, and to flex the knee joint.

2. The method of claim 1, further including adjusting a length of the rigid frame to place the proximal end of the rigid frame above the knee joint.

3. The method of claim 2, wherein adjusting a length of the rigid frame includes sliding one or more telescoping joints within a range of motion, and tightening the one or more telescoping joints at a selected length.

4. The method of claim 3, wherein tightening the one or more telescoping joints at a selected length includes threading one or more collets into a locked position.

* * * * *